US008409636B2

(12) United States Patent
Qu et al.

(10) Patent No.: US 8,409,636 B2
(45) Date of Patent: Apr. 2, 2013

(54) CHIA SEED EXTRACT AND RELATED METHOD OF MANUFACTURE

(75) Inventors: Di Qu, Ada, MI (US); Lisa L. Saito, Winchester, CA (US)

(73) Assignee: Access Business Group International LLC, Ada, MI (US)

(*) Notice: Subject to any disclaimer, the term of this patent is extended or adjusted under 35 U.S.C. 154(b) by 23 days.

(21) Appl. No.: 13/237,541

(22) Filed: Sep. 20, 2011

(65) Prior Publication Data
US 2012/0076876 A1    Mar. 29, 2012

Related U.S. Application Data

(60) Provisional application No. 61/387,646, filed on Sep. 29, 2010.

(51) Int. Cl.
*A61K 36/00* (2006.01)
*A61K 36/537* (2006.01)

(52) U.S. Cl. .................. 424/746; 424/725; 424/776

(58) Field of Classification Search ............... None
See application file for complete search history.

(56) References Cited

U.S. PATENT DOCUMENTS

| | | | |
|---|---|---|---|
| 4,684,522 A | 8/1987 | Marissal et al. | |
| 4,942,033 A | 7/1990 | Aubert et al. | |
| 4,948,583 A | 8/1990 | Grollier et al. | |
| 5,059,426 A | 10/1991 | Chiang et al. | |
| 5,229,130 A | 7/1993 | Sharma et al. | |
| 5,348,943 A | 9/1994 | Pickart | |
| 5,445,822 A | 8/1995 | Bracco | |
| 5,558,871 A | 9/1996 | Griat et al. | |
| 5,716,605 A | 2/1998 | Onitsuka et al. | |
| 5,716,800 A | 2/1998 | Meybeck et al. | |
| 5,747,006 A | 5/1998 | Dornoff et al. | |
| 5,980,904 A | 11/1999 | Leverett | |
| 6,086,861 A | 7/2000 | Onitsuka et al. | |
| 6,348,204 B1 | 2/2002 | Touzan | |
| 6,361,806 B1 | 3/2002 | Allen | |
| 6,403,125 B1 | 6/2002 | Pauly et al. | |
| 6,410,048 B1 | 6/2002 | Fotinos | |
| 6,461,648 B2 | 10/2002 | Soulier et al. | |
| 6,551,625 B1 | 4/2003 | Hilaire et al. | |
| 6,761,913 B2 | 7/2004 | Butters et al. | |
| 6,800,292 B1 | 10/2004 | Murad | |
| 6,994,874 B2 | 2/2006 | Leverett et al. | |
| 7,060,304 B2 | 6/2006 | Leverett et al. | |
| 7,060,693 B1 | 6/2006 | Dumas et al. | |
| 7,108,883 B2 | 9/2006 | Lauria et al. | |
| 7,118,688 B2 | 10/2006 | Mora-Gutierrez et al. | |
| 7,128,914 B2 | 10/2006 | Leclerc et al. | |
| 7,192,616 B2 | 3/2007 | Cals-Grierson et al. | |
| 7,247,321 B2 | 7/2007 | Leverett et al. | |
| 7,364,759 B2 | 4/2008 | Leverett et al. | |
| 7,381,436 B2 | 6/2008 | Andre et al. | |
| 7,402,669 B2 | 7/2008 | Loiseau et al. | |
| 7,638,640 B2 | 12/2009 | Seeram et al. | |
| 7,722,904 B2 | 5/2010 | Schneider et al. | |
| 2002/0168431 A1 | 11/2002 | Belna | |
| 2002/0192178 A1 | 12/2002 | Pelletier et al. | |
| 2004/0208838 A1 | 10/2004 | Leverett et al. | |
| 2004/0208839 A1 | 10/2004 | Leverett et al. | |
| 2006/0099280 A1 | 5/2006 | Shibuya et al. | |
| 2007/0166251 A1 | 7/2007 | Dayan et al. | |
| 2008/0025930 A1 | 1/2008 | Corstjens et al. | |
| 2008/0261291 A1 | 10/2008 | De La Llata Romero | |
| 2008/0305190 A1 | 12/2008 | Vuksan | |
| 2008/0317836 A1 | 12/2008 | Dorogi et al. | |
| 2008/0317933 A1 | 12/2008 | Williamson | |
| 2009/0047310 A1 | 2/2009 | Meybeck | |
| 2009/0117211 A1* | 5/2009 | Schneider et al. ............ 424/747 |
| 2009/0181127 A1 | 7/2009 | Minatelli et al. | |
| 2009/0214628 A1* | 8/2009 | De Rijk ....................... 424/450 |
| 2009/0232785 A1 | 9/2009 | Breton et al. | |
| 2009/0274749 A1 | 11/2009 | Johnson | |
| 2011/0212201 A1* | 9/2011 | Rana et al. .................... 424/769 |

FOREIGN PATENT DOCUMENTS

| | | |
|---|---|---|
| EP | 1140002 | 5/2006 |
| KR | 2008111249 | 12/2008 |
| WO | 0245680 | 6/2002 |

OTHER PUBLICATIONS

Ando et al., Ando, Hideya, et al., "Linoleic Acid and a-Linolenic Acid Lightens Ultraviolet-Induced Hyperpigmentation of the Skin", Arch. Dermatol. Res., 290: 1998, pp. 375-381.

Chang, Te-Sheng, "An Updated Review of Tyrosinase Inhibitors", Int. J. Mol. Sci. vol. 10, 2009, pp. 2440-2475.

Cho, W., et al., "Use of Glycan Targeting Antibodies to Identify Cancer-Associated Glycoproteins in Plasma of Breast Cancer Patients", Anal. Chem. vol. 80:14, Jul. 15, 2008, pp. 5286-5292. Abstract only. http://www.ncbi.nlm.ni.gov/pubmed/18558770.

Khan, Mahmud Tareq Hassan, "Molecular Design of Tyrosinase Inhibitors: A Critical Review of Promising Novel Inhibitors From Synthetic Origins", Pure Appl. Chem. vol. 79, No. 12, 2007, pp. 2277-2295.

Pancheco-Palencia et al. Protective Effects of Standardized Pomegranate (*Punica granatum* L.) Polyphenolic Extract in Ultraviolet-Irradiated Human Skin Fibroblasts, Journal of Agricultural Food Chemistry, (2008), 56, pp. 8434-8441.

Smolinske, Handbook of Food, Drug and Cosmetic Excipients, CRC Press, 1992, p. 307.

The Herbal Encyclopedia, Retrieved from the internet, Retrieved on Apr. 22, 2011, Web archive date Feb. 10, 2003, http://classic-web.archive.org/web/20030210135948/http://www.naturalark.com/herbcomb.html, pp. 1-9.

* cited by examiner

*Primary Examiner* — Qiuwen Mi
(74) *Attorney, Agent, or Firm* — Warner Norcross & Judd LLP

(57) ABSTRACT

Ethanolic chia (*Salvia hispanica*) seed extracts are provided in a system including one or more polyols and at least one hydrophobic compound that solubilize hydrophobic and slightly hydrophilic fractions of the extracts. The polyol can be pentylene glycol. The at least one hydrophobic compound can be a light oil or an ester including, but not limited to, glyceryl caprylate, glyceryl trioctanoate, isodecyl neopentanoate, isononyl isononanoate, isopropyl myristate, phenethyl benzoate, propylene glycol dicaprylate/dicaprate, propylene glycol dioctanoate and combinations thereof. The system or solution can form a cosmetic composition which is highly stable. A method for preparing the composition also is provided.

10 Claims, 6 Drawing Sheets

| Polyols (solvent) | Solubility (5% chia seed extract concentrate) |
|---|---|
| Propylene glycol | Not soluble |
| Butylene glycol | Not soluble |
| Pentylene glycol | Not soluble |
| Hexylene glycol | Not soluble |
| Isoprene Glycol | Not soluble |
| Glycerin | Not soluble |
| Glycereth-26 | Not soluble |

Figure 3

| Light Oils/Esters (solvent) | Solubility (5% Chia seed extract concentrate) |
|---|---|
| C12-15 Alkyl Benzoate | Not soluble |
| C12-15 Alkyl Benzoate (and) Dipropylene Glycol Dibenzoate (and) PPG-15 Stearyl Ether Benzoate | Not soluble |
| Caprylic/Capric Triglyceride | Not soluble |
| Glyceryl Trioctanoate | Not soluble |
| Glyceryl Caprylate | Not soluble |
| Hydrogenated Polyisobutene | Not soluble |
| Isocetyl Stearate | Not soluble |
| Isodecyl Neopentanoate | Not soluble |
| Isohexadecane | Not soluble |
| Isononyl Isononanoate | Not soluble |
| Isopropyl Isostearate | Not soluble |
| Isopropyl Myristate | Not soluble |
| Mineral Oil | Not soluble |
| Neopentyl Glycol Diheptanoate | Not soluble |
| Phenethyl Benzoate | Not soluble |
| Propylene Glycol Dicaprylate / Dicaprate | Not soluble |
| Propylene Glycol Dioctanoate | Not soluble |
| Squalane | Not soluble |

Figure 4

| Light Oils/Esters | Miscibility (polyol and light oil/ester) | | | | | | |
|---|---|---|---|---|---|---|---|
| | Propylene Glycol | Butylene Glycol | Pentylene Glycol | Hexylene Glycol | Isoprene Glycol | Glycerin | Glycereth-26 |
| C12-15 Alkyl Benzoate | No | No | No | Yes | No | No | No |
| C12-15 Alkyl Benzoate (and) Dipropylene Glycol Dibenzoate (and) PPG-15 Stearyl Ether Benzoate | No | No | Yes | Yes | No | No | No |
| Caprylic/Capric Triglyceride | No | No | No | Yes | No | No | No |
| Glyceryl Caprylate | No | Yes | Yes | Yes | Yes | No | No |
| Glyceryl Trioctanoate | No | No | Yes | Yes | No | No | No |
| Hydrogenated Polyisobutene | No | No | No | No | No | No | No |
| Isocetyl Stearate | No | No | No | No | No | No | No |
| Isodecyl Neopentanoate | No | No | Yes | Yes | No | No | No |
| Isohexadecane | No | No | No | No | No | No | No |
| Isononyl Isononanoate | No | No | Yes | Yes | No | No | No |
| Isopropyl Isostearate | No | No | No | Yes | No | No | No |
| Isopropyl Myristate | No | No | Yes | Yes | No | No | No |
| Mineral Oil | No | No | No | No | No | No | No |
| Neopentyl Glycol Diheptanoate | No | Partial | Yes | Yes | No | No | No |
| Phenethyl Benzoate | No | No | Yes | Yes | No | No | No |
| Propylene Glycol Dicaprylate / Dicaprate | No | Partial | Yes | Yes | No | No | No |
| Propylene Glycol Dioctanoate | No | No | Yes | Yes | Partial | No | No |
| Squalane | No | No | No | No | No | No | No |

Figure 5

| Light Oils/Esters | Solubility (5% chia seed extract concentrate) | | | | | | |
|---|---|---|---|---|---|---|---|
| | Propylene Glycol | Butylene Glycol | Pentylene Glycol | Hexylene Glycol | Isoprene Glycol | Glycerin | Glycereth-26 |
| C12-15 Alkyl Benzoate | — | — | No | — | — | — | — |
| C12-15 Alkyl Benzoate (and) Dipropylene Glycol Dibenzoate (and) PPG-15 Stearyl Ether Benzoate | — | — | Yes | No | — | — | — |
| Caprylic/Capric Triglyceride | — | — | No | — | — | — | — |
| Glyceryl Caprylate | — | No | Yes | No | No | | |
| Glyceryl Trioctanoate | — | — | Yes | No | — | — | — |
| Hydrogenated Polyisobutene | — | — | No | — | — | — | — |
| Isocetyl Stearate | — | — | No | — | — | — | — |
| Isodecyl Neopentanoate | — | — | Yes | No | — | — | — |
| Isohexadecane | — | — | No | — | — | — | — |
| Isononyl Isononanoate | No | No | Yes | No | No | No | No |
| Isopropyl Isostearate | — | — | No | — | — | — | — |
| Isopropyl Myristate | — | — | Yes | No | No | No | No |
| Mineral Oil | — | — | No | — | — | — | — |
| Neopentyl Glycol Diheptanoate | — | No | No | — | — | — | — |
| Phenethyl Benzoate | — | — | Yes | No | No | — | — |
| Propylene Glycol Dicaprylate / Dicaprate | — | No | Yes | No | — | — | — |
| Propylene Glycol Dioctanoate | — | — | Yes | No | No | — | — |
| Squalane | — | — | No | — | — | — | — |

Figure 6

CHIA SEED EXTRACT AND RELATED METHOD OF MANUFACTURE

BACKGROUND OF THE INVENTION

The present invention relates to solubilized chia seed extracts and more particularly, to the use of polyols, light oils and/or esters for solubilization of chia seed extracts.

Common chia seed extracts include oils extracted from the seeds of chia by pressing or by solvent extraction. Currently, there are four category entries listed in the Cosmetic, Toiletry and Fragrance Association ("CTFA") Online Ingredient Database under the name of Chia (*Salvia hispanica*) seed for cosmetic applications. These categories include: (1) chia (*Salvia hispanica*) seeds or seed powder, used as abrasives; (2) chia seed oil, used as occlusive skin conditioning agents; (3) chia seed $CO_2$ extract, (with no solvent/diluent, $CO_2$ is a non-polar solvent so due to its selectivity, $CO_2$ extraction usually results in a specific hydrophobic fraction of chia seeds); and (4) chia seed extract solution. There are two water soluble blends of chia seed extract including: HP Chia Seed Gel, manufactured by Morechem Co., Ltd. of Metro Manila, Philippines, which is a mixture of water, butylene glycol and *Salvia hispanica* seed extract; and Chia Extract, which is manufactured by Carrubba, Inc. of Milford, Conn., USA, and which is a mixture of glycerin, water, and *Salvia hispanica* seed extract.

There are a variety of U.S. patents that individually relate to chia seed oil, however, none known to the Applicants show or even contemplate a solubilization or stabilization process that incorporates both polyols and hydrophobic light oils and/or esters. For example, some patents relate to the following: a skin care composition containing chia seed oil for moisturization and appearance of skin; manufacturing conditions of producing chia seed oil containing polyunsaturated fatty acids; cosmetic compositions containing fatty acid triglyceride mixtures from various seeds including chia seeds; use of chia oil in cosmetic and dermatologic compositions containing salicylic acid; use of chia oil as emollient in skin care applications; use of chia oil as one oily component in a film-forming composition for skin care applications; or use of chia oil as an oily component in an antioxidant composition.

SUMMARY OF THE INVENTION

A cosmetic composition including a solubilized chia seed extract and a method of manufacturing the same are provided. In one embodiment, a solubilized chia (*Salvia hispanica*) seed extract composition includes: an ethanolic chia seed extract; at least one polyol; at least one hydrophobic compound selected from the group consisting of esters, light oils and combinations thereof.

In another embodiment, the method includes extracting hydrophobic and slightly hydrophilic components from chia (*Salvia hispanica*) seeds and stabilizing them in a dual-solvent system to achieve a clear and thermodynamically stable solution suitable for use in cosmetic applications, for example, in topical cosmetic compositions used for skin lightening.

In still another embodiment, a method of solubilizing an ethanolic chia (*Salvia hispanica*) seed extract includes: providing an ethanolic chia seed extract; and admixing the chia seed extract in at least one polyol, and at least one hydrophobic compound selected from the group consisting of esters, light oils and combinations thereof, to form a solubilized chia extract.

In yet another embodiment, a composition is provided that is formed by the solubilization steps: providing an ethanolic chia (*Salvia hispanica*) seed extract; and admixing the chia seed extract in at least one polyol and at least one hydrophobic compound selected from the group consisting of esters, light oils and combinations thereof.

In even another embodiment, the polyol is pentylene glycol, and the hydrophobic compound can be selected from the group consisting of glyceryl caprylate, glyceryl trioctanoate, isodecyl neopentanoate, isononyl isononanoate, isopropyl myristate, phenethyl benzoate, propylene glycol dicaprylate/dicaprate, propylene glycol dioctanoate and combinations thereof.

In a further embodiment, the hydrophobic compound is a blend of $C_{12}$-$C_{15}$ alkyl benzoate, dipropylene glycol dibenzoate, and PPG-15 stearyl ether benzoate.

In still a further embodiment, the ratio of pentylene glycol to the hydrophobic compound is from 4:1 to 3:10.

In yet a further embodiment, the ratio of pentylene glycol to the hydrophobic compound is 12:7.

In even a further embodiment, the solubilized chia extract comprises pentylene glycol, isononyl isononanoate, and chia seed extract. The solubilized chia extract can include about 23% to about 80% pentylene glycol, about 20% to about 77% isononyl isononanoate, and about 0.5% to about 20% chia seed extract or optionally 60% pentylene glycol, 35% isononyl isononanoate and 5% chia seed extract.

The current embodiments can efficiently extract hydrophobic and slightly hydrophilic components from chia seeds, and stabilize them in a dual-solvent system to achieve a clear and thermodynamically stable solution suitable for use in cosmetic applications.

These and other objects, advantages and features of the current embodiments will be more readily understood and appreciated by reference to the detailed description of the current embodiments and the drawings.

BRIEF DESCRIPTION OF THE DRAWINGS

FIG. 3 is a table illustrating a solvent system selection of polyols for use in the current embodiment;

FIG. 4 is a table illustrating a solvent system selection of light oils or esters for use in the current embodiment;

FIG. 5 is a table illustrating the miscibility of a polyol and an oil/ester in a dual-solvent system of the current embodiment; and FIG. 6 is a table illustrating the solubility of chia seed extract concentrate in dual-solvent systems of the current embodiment.

DETAILED DESCRIPTION OF THE CURRENT EMBODIMENTS

Figure 1:
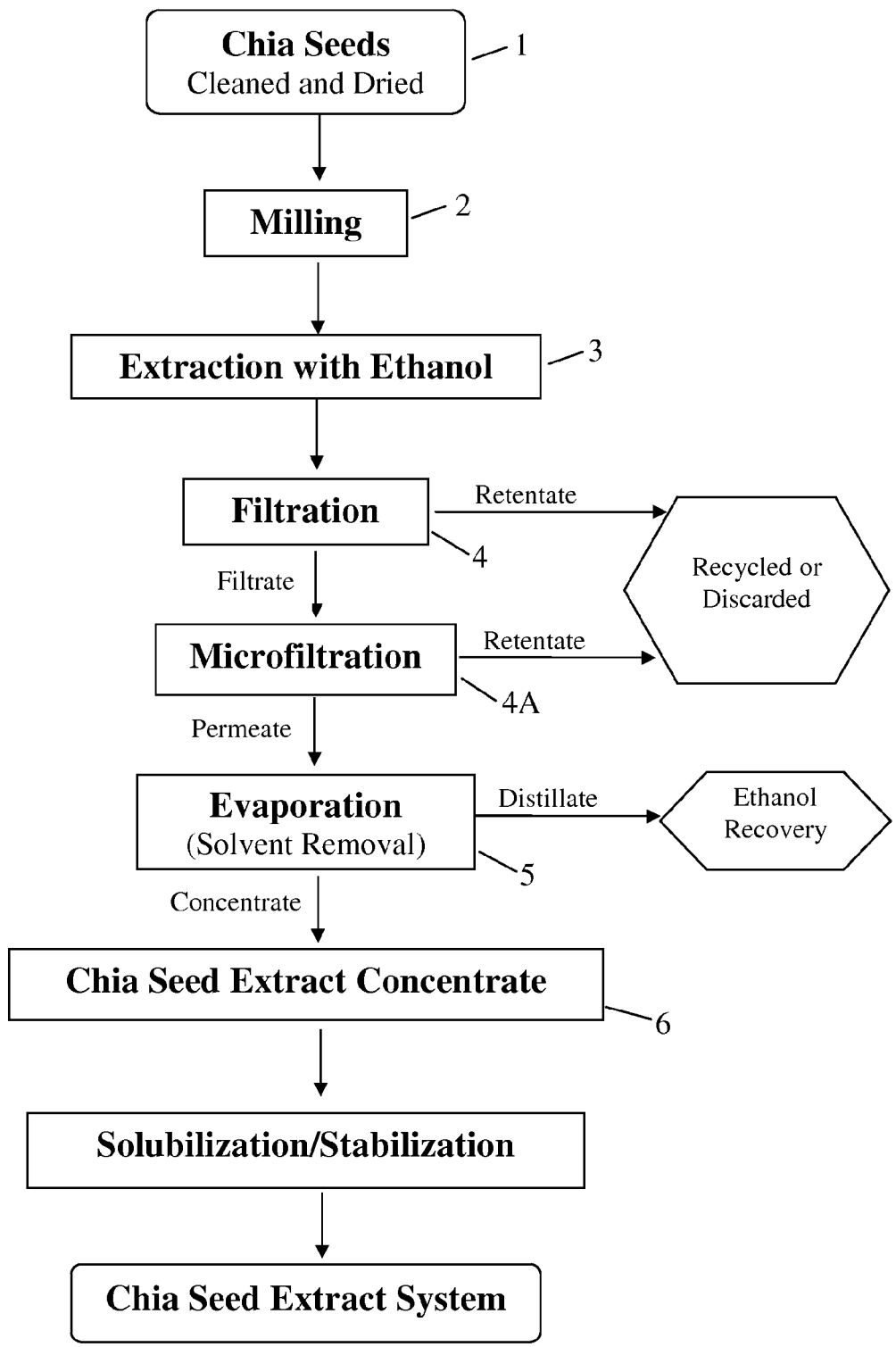
FIG. 1 is a process flowchart for preparing a chia seed extract solution according to a current embodiment.

A current embodiment is described herein in connection with the preparation and use of chia seed extracts. Although described in connection with cosmetic applications, the current embodiments can be used in a variety of other applications.

Chia and its extracts have a variety of beneficial cosmetic uses and activities. For example, chia seed extracts have been demonstrated to have melanin inhibition activity via in vitro efficacy studies, as illustrated in U.S. Patent Publication 2011/0212201 to Rana et al, which is hereby incorporated herein by reference in its entirety. Of course, the extracts of the current embodiments can be used in connection with other beneficial activities.

Certain terms herein have certain meanings unless otherwise specified. For example, the term "chia" as used herein refers to Salvia hispanica. The term "cosmetic" as used herein refers to any preparation designed to beautify, alter the appearance, provide a benefit to a body surface and/or tissue to which it is applied, or to provide a benefit to the subject to which it is applied. Cosmetic can include dermatological and neutraceutical compositions. The term "topical" as used herein refers to being applied directly to the skin. The term "hydrophilic" as used herein refers to being capable of associating with a solution by forming hydrogen bonds with water or other hydrophilic molecules or compounds in the solution, such as alcohols. The terms "hydrophobic" as used herein refers to having little or no affinity for water, or incapable of dissolving to any appreciable extent in water or hydrophilic compound or molecules, for example, alcohols. The term "slightly hydrophilic" refers to a substance that has both hydrophilic and hydrophobic/lipophilic properties, for example, an amphiphilic substance where such a substance can be temporarily solubilized in an oil-based solution by forming relatively unstable bonds or associations with hydrophobic compounds or molecules, but within a short time (e.g., 5 minutes to 5 weeks or more) the substance precipitates out from the solution.

Applicants have discovered that the extraction of whole seeds of chia, with ethanol being the extraction solvent, is complicated by the resulting fractures of the extract. Specifically, both hydrophobic fractions and slightly hydrophilic fractions are extracted from whole seeds of chia. The hydrophobic fraction of the chia seed extract herein includes fats, linolenic acid, linoleic acid, oleic acid, palmitic acid, stearic acid, ferulic acid, and other oil soluble components. The slightly hydrophilic fraction of the chia seed extract includes a variety of alcohol soluble proteins and alcohol soluble polypeptides.

The coexistence of the hydrophobic and the slightly hydrophilic fractions in the ethanolic extract of chia seed presents practical challenges during extraction and formulation stages. For example, the slightly hydrophilic fraction separates from the hydrophobic fraction to form a sticky precipitate in the concentration process after ethanolic extraction. This sticky precipitate sticks to any surface that it contacts when the ethanol is gradually removed, making the slightly hydrophilic fraction less available in final product, which can diminish its intended use and activity. Moreover, in final product, the slightly hydrophilic fraction continues to precipitate gradually over time, e.g., 5 minutes to 5 weeks or more, which leaves a layer of sticky precipitate at the bottom of the associated container. In addition, this precipitate is exceedingly difficult to re-dissolve at the time when the product is to be used in a manufacturing environment. As a result, the slightly hydrophilic fraction is less available, or in some cases unavailable, for use in the final product. Where the final product is a topical cosmetic, this can result in the beneficial slightly hydrophilic fraction of chia being less available, or unavailable, for its intended activity on the skin or other application surface. These technical challenges have made such ethanolic extracts of chia impractical for use in most cosmetic applications.

The current embodiments overcome the above challenges in at least two ways. First, the methods extract both hydrophobic and slightly hydrophilic fractions from chia seeds using ethanol as extracting solvent. The resultant extract provides melanin inhibition efficacy via cell-based in vitro studies. Second, the methods of the current embodiments solubilize and stabilize both the hydrophobic and the slightly hydrophilic fractions in the final extract, which is critical to a commercially viable material suitable for cosmetic applications. Specifically, the dual-solvent system of the current embodiments dissolves both hydrophobic fraction and the sticky, slightly hydrophilic fraction to form a clear (but slightly yellow in color) solution of extract which is thermodynamically stable at room temperature, and which is resistant to precipitation of the slightly hydrophilic fraction of chia. This dual-solvent system produces a chia seed extract that is suitable for cosmetic and other applications.

The composition of the current embodiment includes chia seed extract, which extract can be obtained from a single ethanolic solvent extraction. When extracted, the chia seed can include multiple fractions, but primarily includes a hydrophobic (e.g., lipophilic or oil soluble) fraction and a slightly hydrophilic fraction. It is believed that the single ethanolic extraction of the current embodiment preserves the activity of the fractions, particularly when the extract is used in cosmetic applications.

In the current embodiment, the resulting solubilized chia seed extract system, also referred to as a solution herein, can include the above mentioned chia seed extract, a polyol of the type described herein and an ester and/or light oil as described herein. The chia seed extract can be present in an optional amount of about 0.5% to about 20%, or a further optional amount of about 2% to about 10% by weight (wt/wt) of the solubilized chia seed extract system. The polyol can be present in an optional amount of about 23% to about 80%, or a further optional amount of about 40% to about 70% by weight (wt/wt) of the solubilized chia seed extract system. The ester and/or light oil can be present in an optional amount of about 20% to about 77%, and a further optional amount of about 28% to about 50% by weight (wt/wt) of the solubilized chia seed extract system.

As mentioned above, the solubilized chia seed extract system can include leftover ethanol from an earlier extraction procedure. That ethanol level can be relatively low to reduce the effect of the alcohol on the skin of a user should the solubilized chia seed extract system be further incorporated into a cosmetic composition. For example, the ethanol in the solubilized chia seed extract system can be present in an optional amount of about 0.25% to about 10% by weight (wt/wt) of the solubilized chia seed extract system, or a further optional amount of about 1% to about 5% by weight (wt/wt) of the solubilized chia seed extract system, and an even further optional amount of about 2.5% by weight (wt/wt) of the solubilized chia seed extract system.

Other features of the current embodiments will become apparent in the course of the following descriptions of exemplary embodiments, which are given for illustration of the current embodiments, and are not intended to be limiting thereof. In the following examples, all amounts are given in percent by weight of the solubilized chia seed extract system or solution, that forms the resultant cosmetic composition, unless otherwise specified.

EXAMPLE 1

A solubilized chia seed extract system was obtained from the whole chia seeds. The method for obtaining the solubilized chia seed extract system included the following steps, which are generally illustrated in the flow chart of FIG. 1.

(1) The chia seeds were cleaned and dried. Suitable seeds are *Salvia hispanica* seeds from Nutrilite Farm of El Petecal, Mexico.

(2) The chia seeds were milled with a ball or hammer mill to break and/or fragment the seed material into smaller pieces for extraction.

(3) The milled chia seeds were added to ethanol in an extraction container and extract with 93-95% ethanol at 120° F. (49° C.) for 3 hours, which included a 1 hour hold time, and 2 hours of extraction with agitation. The ratio of ground chia seed:ethanol was 1:10.

(4) The content from the extraction container was filtered through a LIQUATEX Separator fitted with a 325 mesh screen. The separator is commercially available from Rotex, Global, LLC located in Cincinnati, Ohio.

(4A) The liquid filtrate was collected and then underwent a microfiltration step to remove fine, insoluble particulates. The microfiltration unit was equipped with a FP200 (200,000 Molecular Weight) PVDF (polyvinylidene fluoride) tubular membrane. The feed pressure was set at 8-10 bars and the product temperature was 70-80° F. The unit and membranes are commercially available from PCI Membrane Systems located in Hamilton, Ohio. The retentates from these two filtration operations were recovered as by-products and optionally recycled, used as energy or discarded as waste, as indicated in FIG. 1.

(5) The permeate from the microfiltration step was collected and transferred to an evaporator (such as Turbafilm or Centritherm Evaporators) to remove the extraction solvent (ethanol) from the extract solution. Suitable evaporators include a Turba-Film evaporator, available from LCI Corp. of Charlotte, N.C., or a Centritherm evaporator, available from FT Industrial Pty. Ltd of Griffith, Australia. Optionally, the ethanol was recovered for re-use or other use. This operation results in an ethanolic chia seed extract concentrate having an ethanol content controlled at optionally less than 30%, further optionally, less than 20%, by percent weight of the ethanolic extract concentrate. Generally, due to their limited solvency, the hydrophobic and slightly hydrophilic fractions of chia extract were suspended in the extract concentrate to yield a yellowish brown, opaque, and slightly viscous material 104, shown in FIG. 2. This concentrate contained about 50-80% non-volatiles and a suspension of fine particles.

(6) The chia seed extract concentrate was mixed with a dual-solvent system, pentylene glycol and isononyl isononanoate at room temperature 77° F. (25° C.) to obtain a completely dissolved, clear, thin and stable liquid of chia seed extract solution 102, shown in FIG. 2. The resultant composition of this solubilization/stabilization process was a solubilized chia seed extract system or a solution including pentylene glycol: 60%; isononyl isononanoate: 35%; and chia seed extract concentrate: 5%.

In other embodiments beyond the above example, the solubilized chia seed extract system, also referred to as a solubilized and stabilized chia extract composition herein, can include: optionally, about 50% to about 70% polyols and further optionally, about 55% to about 65% polyols; optionally, about 25% to about 45% esters and/or light oils and further optionally, about 30% to about 40% ester and/or light oils; and optionally, about 1% to about 15% chia seed extract concentrate and further optionally about 2% to about 10% chia seed extract concentrate.

The solubilization and stabilization step is considered as the key step in the current embodiment. Due to the unique composition and extraction process, both hydrophobic fractions and slightly hydrophilic fractions in chia seeds are extracted out in the ethanol solution. Moreover, both of these fractions are solubilized within the system, so that the slightly hydrophilic fractions do not precipitate out and/or separate from the solution. In turn, both fractions remain available for use in a cosmetic composition, and both fractions generally remain homogeneously mixed throughout the composition. Thus, when the composition (or some final cosmetic formulation in which the composition is included) is, for example, topically applied to skin, both the hydrophobic and slightly hydrophilic fractions are present in the amount of substance applied so that their activities can be imported to the skin.

Applicants have discovered that another way to maintain solubilization of the hydrophobic and slightly hydrophilic fractions in chia seeds is to have very high ethanol content, for example 80% ethanol; however, this poses flammability concerns and makes a commercial application element nearly impossible. Reducing ethanol levels, however, was presumably thought by Applicants to likely result in solubility concerns, based on the slightly hydrophilic fraction in the extract separating from the solution at low ethanol levels (e.g., less than 60% ethanol), and forming a sticky layer of precipitate which will stick to any surfaces that it contacts. Applicants determined that this solubility issue made it extremely difficult to recover the active fractions and adequately dissolve the active fractions in a cosmetic or other formulation, without the benefit of the current embodiment.

The efficacy of the present dual-solvent system was confirmed after extensive solubility studies. Applicants specifically investigated isononyl isononanoate, which is a light ester, to dissolve lipid soluble materials, and pentylene glycol, which is a polyol that is easily miscible with aqueous solutions, to dissolve hydrophilic and slightly hydrophilic materials. These two solvents are miscible at a wide range of ratios and, as the Applicants discovered, the resulting solution has the unexpected ability to dissolve both the hydrophobic and the slightly hydrophilic fractions in chia seed extracts, and maintain these fractions—and in particular, the slightly hydrophilic fraction in the solution—without that slightly hydrophilic fraction precipitating out, after 5 minutes to 5+ days, or even after a significant storage period of at least six months, or even a year or more, at temperatures ranging from about 65° F. to about 80° F.

Figure 2:
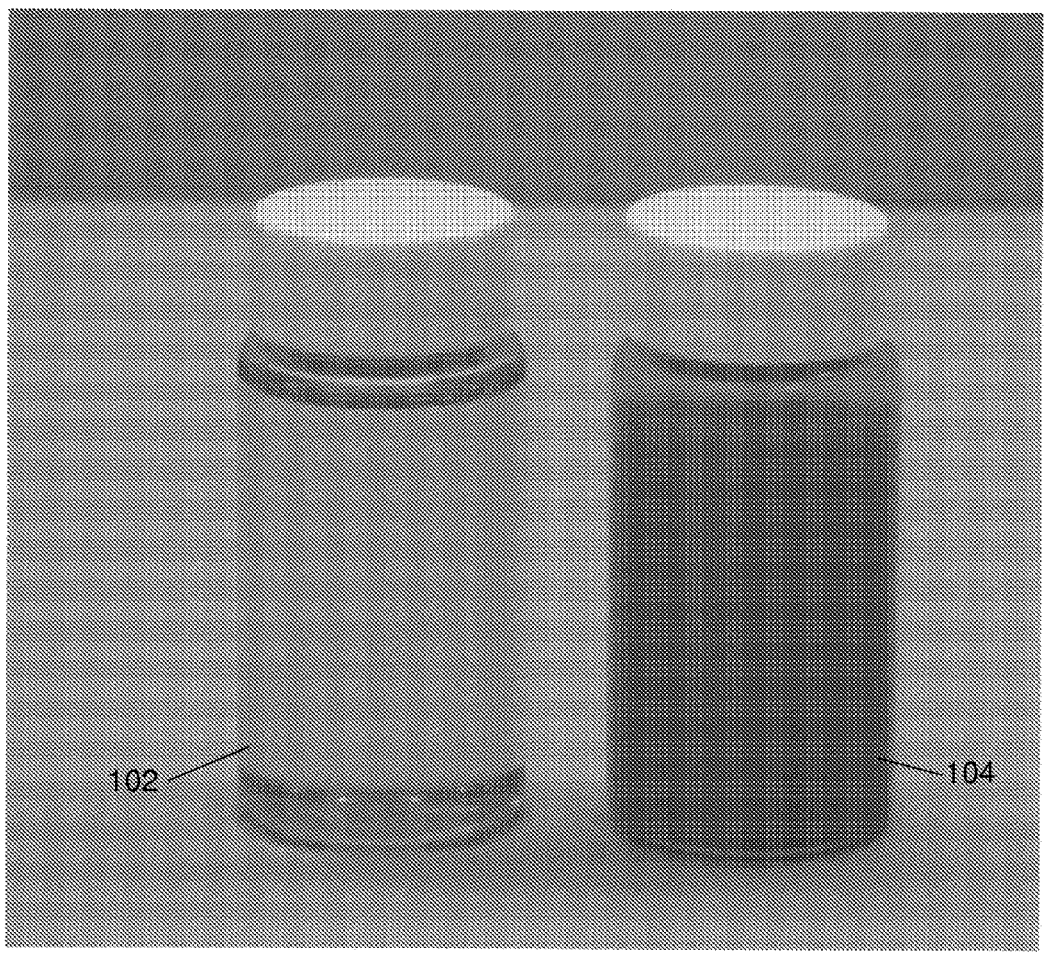
FIG. 2 is an image of a chia seed extract concentrate before solubilization and a chia seed extract after solubilization in a dual-solvent system of the current embodiment.

Again, the resulting solubilized chia seed extract solution 102 is shown in FIG. 2 together with the chia seed extract concentrate 104 before it was solubilized. The resulting solubilized chia seed extract solution 102 is a thin, clear, one-phase, light-yellow liquid which is thermodynamically stable at room temperature storage conditions, for example about 65° F. to about 80° F.

In making the present discovery, many polyols and light esters were evaluated, individually and in combination; however, it was discovered that only a limited number of combinations of polyols and light esters have the ability to solubilize the unique fractions in the chia seed extract. FIGS. 3-6 illustrate the solubilization of ethanolic chia seed extracts using various solvents and their combinations. More particularly, the detailed and self explanatory test results on solubility of single solvent, miscibility of polyol and light oil/ester in a dual-solvent system, as well as the solubility of chia seed extract concentrate in various dual-solvent systems are shown in FIGS. 3-6. Of the polyols tested (glycerin, glycereth-26, propylene glycol, butylene glycol, pentylene glycol, hexylene glycol and isoprene glycol), only pentylene glycol showed the ability to form a dual-solvent system with a limited number of light esters that have the ability to solubilize the complex fractions extracted from chia seeds. Of the light oils/esters tested, there are multiple esters able to form a dual-solvent system with pentylene glycol to adequately dissolve the complex fractions extracted from chia seed. Those light oils/esters include: a commercially available blend of $C_{12}$-$C_{15}$ alkyl benzoate and dipropylene glycol dibenzoate and PPG-15 stearyl ether benzoate; glyceryl caprylate; glyceryl trioctanoate; isodecyl neopentanoate; isononyl isononanoate; isopropyl myristate; phenethyl benzoate; propylene glycol dicaprylate/dicaprate; and/or propylene glycol dioctanoate.

Based on the Applicants' discovery, it was determined that suitable ratios of polyols to the light oils/esters above was from 4:1 to 3:10. This range of ratios was particularly relevant where the polyol was pentylene glycol and the ester was isononyl isononanoate. One particularly suitable ratio of pentylene glycol to isononyl isononanoate was 12:7, at which the polyols and light oils/esters solubilized very well the chia seed extract concentrate fractions, e.g., both the hydrophobic and slightly hydrophobic fractions, in the chia seed extract system or solution.

The resulting solubilized chia seed extract system or solution is well suited for use as a cosmetic composition. The system can be used by itself, or it can be included with other ingredients such as carriers, permeation enhancers and other extracts in a final product cosmetic formulation.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A method of preparing a cosmetic composition comprising:
    providing an ethanolic chia (*Salvia hispanica*) seed extract, the extract including less than 30% ethanol by weight of the ethanolic chia seed extract, a chia seed hydrophobic fraction, and a chia seed slightly hydrophilic fraction; and
    admixing the ethanolic chia (*Salvia hispanica*) seed extract with a polyol and at least one hydrophobic compound to form a solubilized chia extract cosmetic composition,
    wherein the polyol solubilizes a first portion of the chia seed hydrophobic fraction and solubilizes the chia seed slightly hydrophilic fraction,
    wherein the at least one hydrophobic compound is at least one of an ester and a light oil,
    wherein the hydrophobic compound solubilizes a second portion of the chia seed hydrophobic fraction,
    wherein the solubilized chia seed extract cosmetic composition comprises 60% pentylene glycol, 35% isononyl isononanoate, and 5% ethanolic chia (*Salvia hispanica*) seed extract by percent weight of the solubilized chia seed extract cosmetic composition.

2. The method of claim 1 wherein the hydrophobic compound includes the isononyl isononanoate and at least one of glyceryl caprylate, glyceryl trioctanoate, isodecyl neopentanoate, isopropyl myristate, phenethyl benzoate, propylene glycol dicaprylate/dicaprate, propylene glycol dioctanoate and combinations thereof.

3. The method of claim 1 wherein the hydrophobic compound includes isononyl isononanoate blended with at least one of $C_{12}$-$C_{15}$ alkyl benzoate, dipropylene glycol dibenzoate and PPG-15 stearyl ether benzoate and combinations thereof.

4. The method of claim 1 wherein the polyol is pentylene glycol and the hydrophobic compound is isononyl isononanoate.

5. The composition of claim 1 wherein the solubilized chia seed extract cosmetic composition is in the form of a substantially clear, one-phase liquid which is thermodynamically stable when stored between 65° F. and 80° F. for a period of at least six months.

6. A method of preparing a cosmetic composition comprising:
    providing an ethanolic chia (*Salvia hispanica*) seed extract including a chia seed hydrophobic fraction and a chia seed slightly hydrophobic fraction; and
    admixing the ethanolic chia seed extract with a dual solvent system to form a solubilized chia seed extract cosmetic composition, the dual solvent system including at least one polyol that solubilizes the chia seed hydrophobic fraction and the chia seed slightly hydrophobic fraction, the dual solvent system including at least one of an ester and a light oil that solubilizes the chia seed hydrophobic fraction,
    wherein the polyol is pentylene glycol,
    wherein the at least one of an ester and a light oil is isononyl isononanoate, and
    wherein the ratio between pentylene glycol and the isononyl isononanoate is 12:7.

7. The method of claim 6 wherein the solubilized chia seed extract cosmetic composition comprises about 23% to about 80% of the polyol and about 20% to about 77% of the hydrophobic compound by percent weight of the solubilized chia seed extract cosmetic composition.

8. The method of claim 6 wherein the solubilized chia seed extract cosmetic composition includes less than 7% ethanol by percent weight of the solubilized chia seed extract cosmetic composition.

9. The composition of claim 6 further comprising at least one of glyceryl caprylate, glyceryl trioctanoate, isodecyl neopentanoate, isononyl isononanoate, isopropyl myristate, phenethyl benzoate, propylene glycol dicaprylate/dicaprate, propylene glycol dioctanoate, and combinations thereof.

10. The composition of claim 6 wherein the solubilized chia seed extract cosmetic composition is in the form of a substantially clear, one-phase liquid which is thermodynamically stable when stored between 65° F. and 80° F. for a period of at least six months.

* * * * *